ual Patent [19]

Banerjee

[11] Patent Number: 4,692,462
[45] Date of Patent: Sep. 8, 1987

[54] COMPOSITIONS AND METHOD OF CONTROLLING TRANSDERMAL PENETRATION OF TOPICAL AND SYSTEMIC AGENTS

[75] Inventor: Pradip K. Banerjee, King of Prussia, Pa.

[73] Assignee: Menley & James Laboratories, Ltd., Philadelphia, Pa.

[21] Appl. No.: 713,068

[22] Filed: Mar. 18, 1985

[51] Int. Cl.⁴ .................. A61L 15/03; A61F 13/00
[52] U.S. Cl. ............................. 514/449; 424/79
[58] Field of Search ............... 424/28, 79; 514/449

[56] References Cited

U.S. PATENT DOCUMENTS

| | | | |
|---|---|---|---|
| 2,501,927 | 3/1950 | Block | 424/79 |
| 2,684,321 | 7/1954 | Thurmon et al. | 424/79 |
| 2,764,518 | 9/1956 | Thurmon | 424/79 |
| 2,823,163 | 2/1958 | Thoms | 424/79 |
| 2,838,440 | 6/1958 | Thurmon | 424/79 |
| 2,857,311 | 10/1958 | Thurmon et al. | 424/79 |
| 2,883,324 | 4/1959 | Thurmon | 424/79 |
| 2,919,230 | 12/1959 | Thurmon | 424/79 |
| 2,951,012 | 8/1960 | Gisvold | 424/79 |
| 3,567,820 | 3/1971 | Sperti | 424/79 |
| 3,922,342 | 11/1975 | Rathbon | 424/79 |
| 3,922,723 | 12/1975 | Popper | 424/79 |

FOREIGN PATENT DOCUMENTS

| | | | |
|---|---|---|---|
| 21318 | 2/1982 | Japan . | |
| 8203770 | 11/1982 | PCT Int'l Appl. | 424/79 |
| 711886 | 7/1954 | United Kingdom | 424/79 |
| 552083 | 4/1977 | U.S.S.R. | 424/79 |
| 833240 | 5/1981 | U.S.S.R. | 424/79 |

*Primary Examiner*—Shep K. Rose
*Attorney, Agent, or Firm*—Joseph A. Marlino; Stuart R. Suter; Alan D. Lourie

[57] ABSTRACT

Compositions and methods useful for improved and controlled transdermal and transmembrane drug delivery of topical and systemic agents. The compositions and methods comprise a pharmacologically active drug together with a non-toxic pharmaceutically acceptable ion exchange resin, and a salt in a gel-forming vehicle and topically administering to human or animal skin or other membranes the resulting compositions. If desired, a penetration enhancer may also be employed in the compositions of this invention.

11 Claims, 5 Drawing Figures

COMPOSITIONS AND METHOD OF CONTROLLING TRANSDERMAL PENETRATION OF TOPICAL AND SYSTEMIC AGENTS

This invention relates to compositions and a method for the transdermal drug delivery of topical and physiologically active agents. More specifically, this invention relates to improved compositions for topical application and a method for controlling the transdermal and transmembrane penetration of pharmacologically active substances by using an ion exchange resin-drug complex.

Since the skin is the largest and most accessible tissue for drug delivery, transdermal delivery systems are finding more applications for the administration of pharmacologically active substances. Due to this potential usefulness of skin as a route of drug administration for systemic therapy, the technology in this area is rapidly advancing.

An effective transdermal route of drug delivery can provide many advantages over the oral route. Side effects associated with the oral route of administration could be diminished or overcome. For example, a first pass metabolism can be avoided, i.e., reduction of metabolism due to an initial bypass of the liver. The transdermal route of entry could provide the ability to control the administration of drugs that have a small therapeutic index, i.e., drugs that have a narrow range between their therapeutic and toxic levels. A further advantage is that the transdermal route avoids the gastrointestinal tract and the side effects arising from gastrointestinal disturbances. A still further advantage would be the targeting of the drug to dermal and subdermal tissue sites, i.e., delivering the drug directly into the systemic circulation.

Because of the above listed potential advantages of transdermal drug delivery, researchers have long sought an effective means of introducing drugs into the systemic circulation by applying them to the unbroken skin. However, the skin presents a formidable barrier to drug penetration. These barrier properties reside principally in the stratum corneum, the outermost layer composed of close packed dead keratinized cells. The penetration of the substances applied to the skin surface is inversely related to the thickness of the stratum corneum layer.

Many attempts to control the penetration of pharmacologically active drugs both locally and through the skin have been made. The more popular approach has been the employment of surface active or other penetrating agents. However, many of these agents control the permeability by actually damaging the barrier tissue and cause undesirable side effects.

Other prior art methods of controlling transdermal penetration of active substances are the use of different polymeric matrices and employment of a series of rate limiting membranes to help control the release of the active ingredient. Further, one of the disadvantages of the prior methods and compositions for transdermal delivery permit the use of only one active ingredient. It is not possible to vary the release rate of two or more drug molecules independently of each other.

It is therefore an object of this invention to provide improved compositions for topical application and provide a method of controlling transdermal and transmembrane penetration of pharmacologically active drugs without adverse side effects, systemically or locally, on the skin or body membranes.

It is a still further object of this invention to provide compositions and a method which can also deliver transdermally two or more different drugs at different rates independently of each other.

These and other objects are attained by the use of compositions and a method as described in more detail below.

The novel compositions of this invention can deliver different drug molecules at different rates and do not need an additional membrane for controlling the rate of release. Prior art systems can not vary release rates of drug molecules independently of each other.

The compositions of this invention contain a safe and effective amount of a pharmacologically active drug bonded to an ion exchange resin. The drug-ion exchange resin complex may have the resin loaded with one or more drugs. The drug loaded resin is mixed with a salt and dispersed in a gel-forming vehicle.

According to this invention the release rate may be controlled by choosing the appropriate salt for the transdermal composition. Since different salts have different equilibrium relative humidity, the water loss in these compositions may be altered. The body continuousy loses water through the skin (trans epidermal water loss). This water loss varies, depending on temperature, humidity, disease conditions, etc. The system described herein is novel in that multiple drug molecules may be bound onto resins of different structures and each molecule can be released from the complex at rates independent of each other and individually controllable. By appropriate choice of salt, gel material and ion exchange resin, it is possible to make the release rate dependent or independent of body water loss.

Any nontoxic pharmaceutical grade ion-exchange resin used to bind both cationic and anionic drug molecules at the ion exchange sites may be employed in this invention. For example, any wide range of cationic (for basic pharmacological agents) or anionic (for acidic agents) ion exchange resins can be employed. Examples of cationic resins would be weak acid cation exchange resins with the functional moiety being a carboxylic acid (—COOH) group. This could be derived from polymers or copolymers such as methacrylic acid or polymethacrylate. A strongly acidic cation exchange resin having the functional group —SO$_3$Na derived from the polymer styrene could also be employed. Examples of anionic resins are those having the functional group NH,NH$_2$ which are weakly basic and could be derived from phenolic polyamines or the strongly basic type having as the functional group —N(R)$_3$ also derived from polystyrenes.

The above ion exchange resins are well known as the amberlite class, such as, for example, Amberlite IR-120, Amberlite IRP-64, Amberlite IRP-58, or Amberlite IRC-50.

Drugs which may be employed with the cationic ion exchange resins may be, for example, pseudoephedrine, ephedrine, chlorpheniramine, dextromethorphan, phenylpropanolamine, phenylephrine, propylhexedrine, and propranolol. Examples of drugs that may be used with anionic ion exchange resins are the carboxylic type such as aspirin or indomethacin, or acetaminophen, para-aminosalicylic acid.

Appropriate gel-forming substances which may be employed in the composition of this invention are gelatin, polyvinylalcohol, agarose, hydroxypropyl cellulose, hydroxypropyl methylcellulose, hydroxyethyl cellulose polyacrylamide, gum arabic, agar, polyvinylpyrrolidone and quaternary nitrogen containing cellulose ethers known as Ucare polymers described in U.S. Pat. No. 3,472,840.

Any organic or inorganic salt containing the appropriate counter ion for the ion exchange resin can be employed. For example, if an anionic ion exchange resin is employed, a salt containing a positive charged ion would be used, i.e., $Na^+$.

Exemplary of salts that may be used in this invention are sodium chloride, monobasic sodium phosphate, dibasic sodium phosphate, zinc sulfate, magnesium chloride, calcium chloride, potassium chloride, sodium sulfate, sodium acetate, magnesium acetate and sodium citrate.

Adsorption of drugs onto ion exchange resins is well known to the art as demonstrated in U.S. Pat. Nos. 2,990,332 and 4,221,778.

Generally the ion exchange resin is washed in deionized water and treated with sodium hydroxide to convert the resin to the sodium form. The excess sodium hydroxide in the resin is removed by washing with deionized water. The resin is then placed in a glass column and an aqueous solution of the drug is passed through the column.

Alternatively, the resin may be mixed with deionized water and the drug added with mixing. The drug-resin complex is filtered and dried.

In order to help facilitate the penetration of the active ingredient through the skin, agents such as decylmethylsulfoxide, dimethylsulfoxide or other known enhancers may be employed.

The drug-resin complex and the desired salt and a penetrating agent, if desired, are mixed with deionized water containing a gel-forming polymer.

The gel matrix is then poured in a cavity of inert material to form the transdermal device.

As a preferred embodiment in the packaging of the ion exchange matrix, the drug-salt-ion exchange composition is poured in a cavity provided with an inert backing material such as a plastic film which does not permeate a medicine. Exemplary of such backing members are metallic foils such as aluminum foil, polyolefins such as polyethylene and polypropylene, polyesters such as polyethylene terephthalate, polyamides such as nylon and the like. The drug containing composition is permitted to cool and gel or solidify in the cavity. Preferably a gel is formed. An adhesive layer is provided on the backing material surrounding the cavity. To prevent loss in the surface of the composition, the adhesive layer and matrix are sealed with a protective peel off cover sheet.

To use the device, the patient peels off the release layer and places the device in intimate contact with the skin. The exposed adhesive layer secures the device to the patient.

A detailed description and better understanding of this invention can be had by referring to the accompanying drawings which show a preferred embodiment of the present invention.

Figure 1:
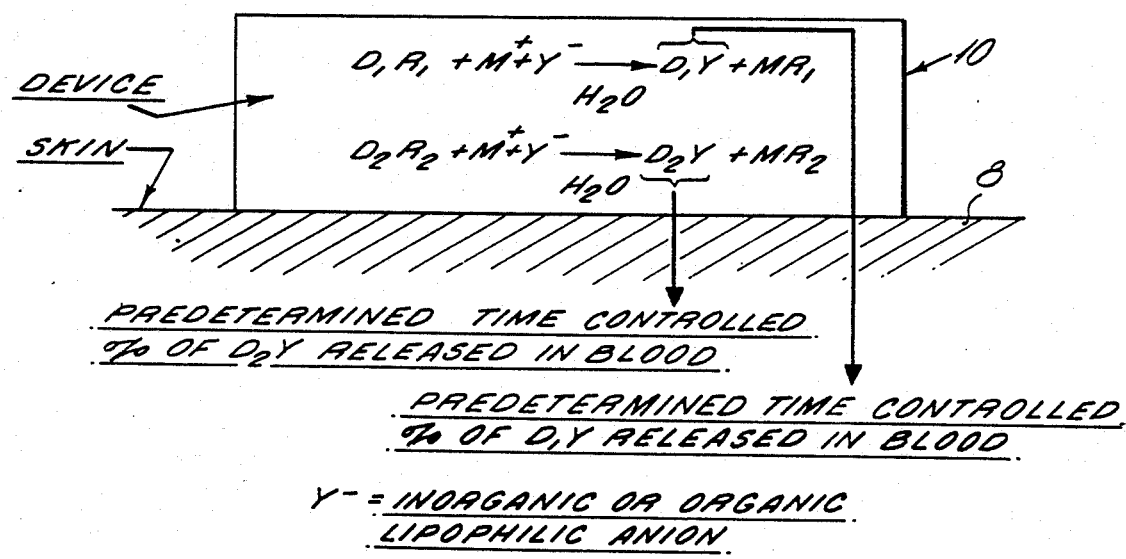
FIG. 1 is a diagramatic schematic view illustrating the mechanism for a multi-medicated transdermal composition.

FIG. 1 demonstrates the drug-resin complex formation taking place in the transdermal composition. It will be noted that the drug $D+X$ is reacted with the resin NaR to yield the drug-resin complex DR plus a salt NaX. This reaction can be accomplished with two different drugs, $D_1$, $D_2$. The drug-resin complexes $D_1R_1$ and $D_2R_2$ are then mixed with the desired salt $M^+ + Y^-$ in the presence of water which results in a new salt form of the drug $D_1Y$, $D_2Y$ and resins $MR_1$ and $MR_2$. The above composition is placed in a cavity of device 10 as described hereinabove. When device 10 is placed on skin 8 the two different drug molecules penetrate the skin and are released independently. The drug release is dependent on the salt employed.

Figure 2:
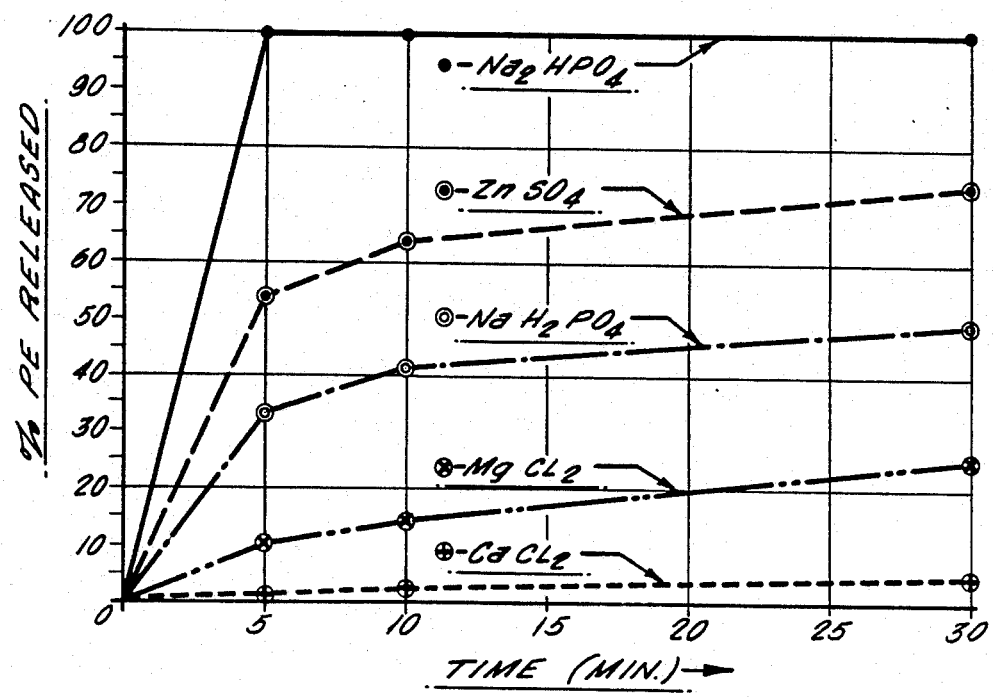
FIG. 2 is a graph showing percent of drug released plotted against time utilizing various salts.

FIG. 2 is a graph which demonstrates how the release of a drug-resin complex is controlled by different saturated salt solutions. In this case the drug PE is pseudoephedrine and the resin IRP 64 is a weak acid ($-COOH^+$) cation exchange resin known as Amberlite. It will be noted that calcium chloride ($CaCl_2$) releases about 5% in 30 minutes, zinc sulfate ($ZnSO_4$) releases about 70% in 30 minutes, and dibasic sodium phosphate ($NaHPO_4$) releases 100% pseudoephedrine in 5 minutes. FIG. 2 also discloses how the addition of monobasic sodium phosphate ($NaH_2PO_4$) and magnesium chloride ($MgCl_2$) control the release rate.

Figure 3:
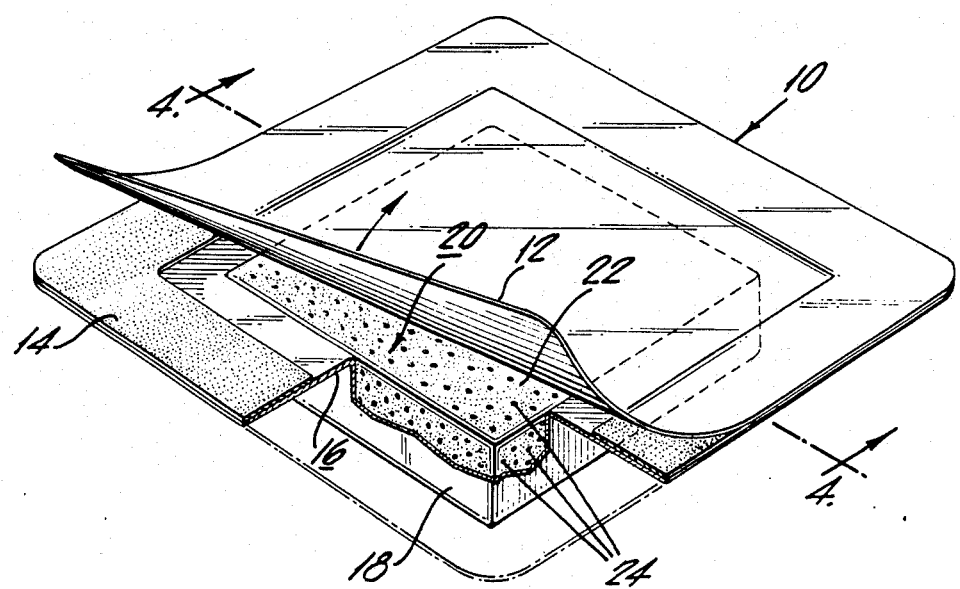
FIG. 3 is an enlarged perspective view showing details of a preferred device of this invention.

Referring to FIG. 3, a device 10 is provided with a cavity 18 having inert backing material 16. The cavity contains composition 20 comprising salts, a gel-forming polymer, water and resin-drug complexes 22 and 24. An adhesive layer 14 is provided on the backing material surrounding the cavity. A protective peel off cover sheet 12 seals the adhesive material and matrix in order to prevent loss in the surface of the matrix.

To use the device the patient peels off the protective cover 12 and places the device in intimate contact with the skin. The now exposed adhesive layer secures the device to the patient's skin. By providing a surface of adhesive around the periphery of the backing material, a liquid tight adhesive seal between the bandage and the patient's skin is maintained. The drug may be directly absorbed by the skin without first migrating through an adhesive layer. In this fashion, the adhesive need not be permeable to the passage of the drug.

Figure 4:
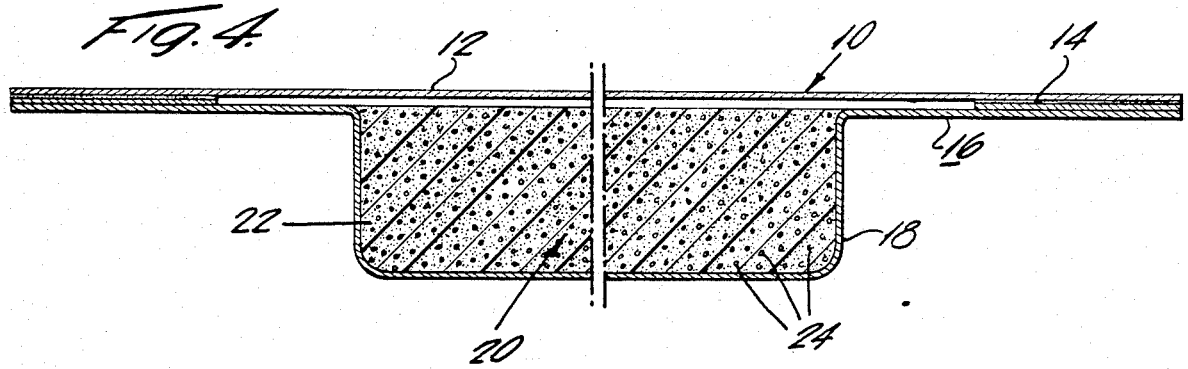
FIG. 4 is an enlarged sectional view taken on the line 4,4 of FIG. 3.
Figure 5:
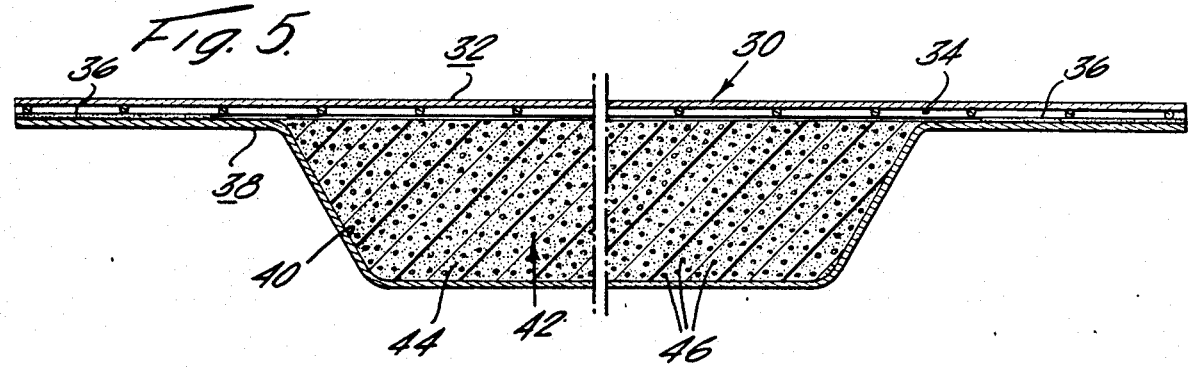
FIG. 5 is a view illustrating a modified form of FIG. 4.

FIG. 5 represents a modification of FIG. 4 wherein a protective membrane 34 is added to device 30. Advantageously this membrane is employed to help prevent the gel polymer from seeping out of the device and is not used as a rate controlling membrane for the drug. In this modification the device also has a cavity 40 containing the composition comprising a gel polymer, water, salts and drugs 44 and 46.

The drug-resins are ground and mixed with an inorganic salt. The mixture is incorporated into an appropriate gel-forming vehicle.

The device is also provided with backing member 38, adhesive layer 36 along the periphery of the backing member and a protective peel off sheet 32.

More specifically, the following examples which are not limiting are illustrative of the methods for preparing the compositions of this invention.

EXAMPLE 1

Drug-Resin Complexes 100 gms. of Amberlite IRC-50, a weakly acidic cationic ion exchange resin, was washed in 2 l. of deionized water. The resin was converted to the sodium form by treating with 5 vol. of sodium hydroxide for four hours. The excess sodium hydroxide was removed by washing with several volumes of deionized water. The resin was then placed in a glass column and 200 mg./ml. of pseudo-ephedrine-water solution (25 vol./1 gm. of resin) was passed through the column at 1 ml./min. $Cm^2$.

Gel Formation

Ucare Jr. 125, a cationic quaternary-nitrogen containing cellulose ether polymer (15 gms.) was mixed with 10 gms. of sodium chloride and 5 gms. of pseudoephedrine in 100 ml. of deionized water and made into a gel by heating for about six hours at 50° C.

25 gms. of the pseudoephedrine-ion exchange resin was gently mixed with 75 gms. of the gel and poured into a plastic cavity and allowed to cool to form a device for transdermal delivery.

EXAMPLE 2

The simultaneous loading of pseudoephedrine and chlorpheniramine was performed by passing aqueous solutions of 200 mg./ml. of pseudoephedrine and 50 mg./ml. of chlorpheniramine through an Amberlite IRC-50 resin column as prepared in Example 1 at a flow of 1 ml./min. $Cm^2$.

50 gms. of the combined pseudoephedrine-chlorpheniramine ion exchange resin was mixed with 150 gms. of the gel as prepared in Example 1 and poured into a cavity with an inert backing member to form a device for transdermal delivery.

EXAMPLE 3

Phenylpropanolamine-Resin Complex 216 gms. of Amberlite IR-120 are placed in 700 ml. of deionized water in a suitable container and mixed for twenty minutes. 105 gms. of phenylpropanolamine base is gradually added with mixing. The drug-resin complex is filtered and dried.

Both the phenylpropanolamine-resin complex and the pseudoephedrine-resin complex, as prepared in Example 1, are gently mixed in the gel matrix of Example 1.

The gel composition containing two different active ingredients is poured into a cavity as described hereinbefore to form a device for transdermal delivery.

What is claimed is:

1. A pharmaceutical composition for the controlled transdermal delivery of one or more pharmacologically active systemic drugs comprising a safe and effective amount of a systemic drug-ion exchange resin complex and a salt effective to control the drug release note, containing the appropriate counter ion for the ion-exchange resin, selected from the group consisting of sodium chloride, monobasic sodium phosphate, dibasic sodium phosphate, zinc sulfate, magnesium chloride, calcium chloride, potassium chloride, sodium sulfate, sodium acetate, magnesium acetate and sodium citrate in a gel-forming vehicle.

2. The composition of claim 1 wherein the drug is pseudoephedrine.

3. The composition of claim 1 wherein the ion exchange complex contains the systemic drugs pseudoephedrine and chlorpheniramine.

4. The composition of claim 1 wherein the ion exchange resin is a carboxylic acid resin.

5. The composition of claim 4 wherein the salt is sodium chloride.

6. The composition of claim 1 in which the gel-forming vehicle comprises the gel-forming substances selected from the group consisting of gelatin, hydroxypropyl methylcellulose, polyvinylpyrrolidone and a quaternary nitrogen containing cellulose ether mixed with water.

7. A method for controlling the transdermal penetration of one or more non-toxic pharmacologically active systemic drugs to a patient which comprises applying to said patient a composition comprising a systemic drug-ion exchange resin complex and a salt effective to control the drug release note, containing the appropriate counter ion for the ion-exchange resin, selected from the group consisting of sodium chloride, monobasic sodium phosphate, dibasic sodium phosphate, zinc sulfate, magnesium chloride, calcium chloride, potassium chloride, sodium sulfate, sodium acetate, magnesium acetate and sodium citrate in a gel-forming vehicle.

8. The method of claim 7 wherein the ion exchange complex contains the systemic drugs pseudoephedrine and chlorpheniramine.

9. In a device for use in the controlled transdermal delivery of pharmacologically active systemic drugs provided with a cavity having an inert backing member which is impermeable to said systemic drugs, the improvement comprising said cavity containing a composition comprising a systemic drug-ion exchange resin complex and a salt effective to control the drug release note, containing the appropriate counter ion for the ion-exchange resin, selected from the group consisting of sodium chloride, monobasic sodium phosphate, dibasic sodium phosphate, zinc sulfate, magnesium chloride, calcium chloride, potassium chloride, sodium sulfate, sodium acetate, magnesium acetate and sodium citrate in a gel-forming vehicle.

10. A device for use in the controlled transdermal administration of pharmacologically active systemic drugs comprising a cavity, a backing member impermeable to said systemic drugs surrounding said cavity, an adhesive layer on said backing member, said cavity containing a composition comprising a systemic drug ion exchange resin complex and a salt effective to control the drug release note, containing the appropriate counter ion for the ion-exchange resin, selected from the group consisting of sodium chloride, monobasic sodium phosphate, dibasic sodium phosphate, zinc sulfate, magnesium chloride, calcium chloride, potassium chloride, sodium sulfate, sodium acetate, magnesium acetate and sodium citrate in a gel forming vehicle which provides a controlled rate of systemic drug release.

11. The device of claim 10 in which the backing member is a plastic film.

* * * * *